(12) United States Patent
Bertrand et al.

(10) Patent No.: US 9,364,646 B2
(45) Date of Patent: *Jun. 14, 2016

(54) TOOL FOR ADJUSTING AN IMPLANTABLE ADJUSTABLE FLUID FLOW CONTROL VALVE

(71) Applicant: Medtronic, Inc., Minneapolis, MN (US)

(72) Inventors: William J. Bertrand, Ventura, CA (US); Leanne M. Lintula, Santa Barbara, CA (US); Leonard Porche, Simi Valley, CA (US)

(73) Assignee: Medtronic, Inc., Minneapolis, MN (US)

( * ) Notice: Subject to any disclaimer, the term of this patent is extended or adjusted under 35 U.S.C. 154(b) by 10 days.

This patent is subject to a terminal disclaimer.

(21) Appl. No.: 14/148,151

(22) Filed: Jan. 6, 2014

(65) Prior Publication Data

US 2014/0121586 A1 May 1, 2014

Related U.S. Application Data

(63) Continuation of application No. 09/745,108, filed on Dec. 20, 2000, now Pat. No. 8,622,978, which is a continuation of application No. 09/270,540, filed on Mar. 17, 1999, now abandoned.

(51) Int. Cl.
*A61M 27/00* (2006.01)
*A61B 19/00* (2006.01)
*A61M 39/02* (2006.01)
*A61M 5/42* (2006.01)

(52) U.S. Cl.
CPC .............. *A61M 27/006* (2013.01); *A61B 19/22* (2013.01); *A61B 19/46* (2013.01); *A61M 5/42* (2013.01); *A61M 2039/0238* (2013.01); *A61M 2205/3515* (2013.01); *A61M 2209/04* (2013.01)

(58) Field of Classification Search
CPC .............. A61M 2205/3515; A61M 2205/353; A61M 2205/3538; A61M 2039/0238; A61M 27/006; A61M 5/42; A61M 5/425; A61M 5/427; F16K 31/086; F16K 31/088
USPC ............................ 604/8–10, 93.01, 246–248, 604/288.01–288.04
See application file for complete search history.

(56) References Cited

U.S. PATENT DOCUMENTS 4,156,422 A * 5/1979 Hildebrandt ........ A61M 27/006
600/561
4,360,007 A * 11/1982 Levy ..................... A61F 2/0036
128/899

(Continued)

*Primary Examiner* — Andrew Gilbert
(74) *Attorney, Agent, or Firm* — Harness, Dickey

(57) ABSTRACT

Tools for determining and adjusting the setting of an adjustable valve are disclosed. These tools allow a medical professional to locate and non-invasively determine the setting of an implanted valve. After the valve has been located and the setting of the valve determined, the valve may be re-adjusted non-invasively. There are three tools: a locator tool, an indicator tool and an adjustment tool. The locator tool allows the physician to locate the adjustable valve of interest and align the locator tool with a specific orientation of the valve. The indicator tool indicates the current setting of the adjustable valve and confirms new settings of the valve after the new settings have been implemented. The adjustment tool interacts magnetically with the implanted adjustable valve to couple with a movable internal element to change the setting of the valve. The indicator tool and the adjustment tool physically cooperate with the locator tool to accomplish the respective functions of the tools.

19 Claims, 6 Drawing Sheets

(56) References Cited

U.S. PATENT DOCUMENTS

| | | | | |
|---|---|---|---|---|
| 4,438,568 A * | 3/1984 | Kramer | G01C 17/04 | 33/272 |
| 4,540,400 A * | 9/1985 | Hooven | F16K 15/144 | 251/65 |
| 4,595,390 A * | 6/1986 | Hakim | A61F 2/0036 | 137/530 |
| 4,608,992 A * | 9/1986 | Hakim | A61B 5/031 | 600/431 |
| 4,615,691 A * | 10/1986 | Hakim | A61F 2/0036 | 310/181 |
| 4,676,772 A * | 6/1987 | Hooven | A61M 27/006 | 116/204 |
| 5,281,199 A * | 1/1994 | Ensminger | A61M 39/0208 | 604/288.03 |
| 5,342,311 A * | 8/1994 | Dirina | A61M 5/00 | 128/919 |
| 5,527,277 A * | 6/1996 | Ensminger | A61M 39/0208 | 604/116 |
| 5,620,419 A * | 4/1997 | Lui | A61M 5/427 | 604/116 |
| 5,637,083 A * | 6/1997 | Bertrand | A61M 27/006 | 604/248 |
| 5,643,194 A * | 7/1997 | Negre | A61M 27/006 | 137/385 |
| 5,928,182 A * | 7/1999 | Kraus | A61M 27/006 | 604/9 |
| 6,050,969 A * | 4/2000 | Kraus | A61M 27/006 | 600/12 |
| 7,044,932 B2 * | 5/2006 | Borchard | A61M 5/14276 | 604/116 |
| 7,921,571 B2 * | 4/2011 | Moureaux | A61M 27/006 | 128/899 |
| 8,038,641 B2 * | 10/2011 | Soares | A61B 5/031 | 251/292 |
| 8,322,365 B2 * | 12/2012 | Wilson | A61M 27/006 | 137/530 |
| 8,622,978 B2 * | 1/2014 | Bertrand | A61M 27/006 | 604/248 |
| 8,733,394 B2 * | 5/2014 | Negre | A61M 27/006 | 137/551 |
| 9,126,010 B2 * | 9/2015 | Shah | F16K 37/0008 | |
| 9,216,275 B2 * | 12/2015 | Soares | A61M 27/006 | |
| 2002/0022793 A1 | 2/2002 | Bertrand et al. | | |

* cited by examiner

TOOL FOR ADJUSTING AN IMPLANTABLE ADJUSTABLE FLUID FLOW CONTROL VALVE

CROSS-REFERENCE TO RELATED APPLICATIONS

This application is a continuation of U.S. patent application Ser. No. 09/745,108 filed on Dec. 20, 2000, now U.S. Pat. No. 8,622,978, which is a continuation of U.S. patent application Ser. No. 09/270,540 filed on Mar. 17, 1999, now abandoned. The entire disclosures of the above applications are incorporated herein by reference.

FIELD

The present disclosure relates to surgically implanted physiological shunt systems and related flow control devices. More particularly, the present invention relates to a position indicator and adjustment tool for such shunt systems having variable pressure settings for the one-way flow control valves controlling the flow of Cerebral Spinal Fluid (CSF) out of a brain ventricle and preventing backflow of fluid into the brain ventricle.

BACKGROUND

This section provides background information related to the present disclosure which is not necessarily prior art.

A typical adult has a total of about 120-150 cc of CSF with about 40 cc in ventricles in the brain. A typical adult also produces about 400-500 cc/day of CSF, all of which is reabsorbed into the blood stream on a continuous basis.

Sometimes, the brain produces excess CSF. One common cause of the excess production of CSF is hydrocephalus. Hydrocephalus is a condition of excessive accumulation of CSF in the ventricles or brain tissue. Hydrocephalus can result from genetic conditions or from trauma to the brain.

Excessive accumulation of CSF, due to hydrocephalus or other causes, manifests itself as increased pressure within the brain. Whatever the cause, over time, this increased CSF pressure causes damage to the brain tissue. It has been found that relieving the CSF pressure is therapeutically beneficial. This is usually done by draining CSF from the ventricles.

Patients with hydrocephalus often continue to produce excess CSF, at least over some time period. Therefore, it is often desirable to continuously drain excess CSF to maintain normal CSF pressure in the brain. Excessive CSF accumulated in the ventricles of the brain is typically drained away from the brain using a shunt system.

Where hydrocephalus is a chronic condition, the shunt system typically drains the CSF into the patient's peritoneal cavity or into the patient's vascular system. Such shunt systems typically have a catheter implanted in the ventricle of the brain. The catheter is connected to a fluid control device which is in turn connected to a catheter which empties in to the patient's peritoneal cavity or into the patient's vascular system.

An example of a fluid control device is shown in U.S. Pat. No. 5,637,083 issued to William J. Bertrand and David A. Watson on Jun. 10, 1997 entitled "Implantable Adjustable Fluid Flow Control Valve", the teaching of which is incorporated herein in its entirety by reference. The valve of the '083 patent is shown in FIGS. 1-3 generally labeled 10 (20). (Reference numbers in parentheses correspond to the reference numbers in the '083 patent. After the corresponding reference number to the '083 patent has been given once, no further reference to the '083 will be given although the connection to the '083 patent is intended to be implied throughout this description.) The valve 10 includes a an inlet connector 12 (22) and an outlet connector 14 (24). A elastomeric casing 16 (30) covers the inner workings of the valve 10. A dome 18 (60) extends upward from the elastomeric casing 16. Fluid flows through the valve 10 in the direction indicated by the arrow "A".

Valve 10 includes a mechanism to control fluid flow through the valve 10. The mechanism includes a magnet 20 (120) embedded within a base 22 (122). Rotating the base 22 changes the internal configuration of the mechanism. Changing the internal configuration of the mechanism produces a variety of pressure or flow characteristics for the valve. The base 22 may be rotated by magnetically coupling an external magnet 24 (140) to the valve's magnet 20 and rotating the external magnet 24. Because magnet 20 is coupled to the external magnet 24, when magnet 24 rotates, magnet 20 also rotates. As magnet 20 rotates, base 22 rotates and the internal configuration of the mechanism changes as described in detail in the '083 patent. As the internal configuration of the valve 10 changes, the pressure/flow characteristics of the valve 10 change. In use, the valve 10 is subcutaneously placed on the patient's skull. The catheter going to the patient's ventricle in attached to inlet connector 12. The catheter going to the patient's peritoneal cavity or vascular system is attached to outlet connector 14. In this way, a direction of flow is established from the inlet connector 12 through the valve 10 to the outlet connector 14. As stated above and described in detail in the '083 patent, changing the internal configuration of the mechanism by coupling the external magnet to the internal magnet and rotating the base produces a variety of pressure or flow characteristics through the valve 10.

A problem with current adjustable valves, such as the one described in the '083 patent is that once implanted, it is difficult to determine the setting of the valve. Further, it is difficult to adjust the setting of the valve. With some adjustable valves, x-ray images are used to determine the current state or post adjustment state of the valve.

SUMMARY

This section provides a general summary of the disclosure, and is not a comprehensive disclosure of its full scope or all of its features.

Tools for determining and adjusting the setting of an adjustable valve are disclosed. These tools allow a medical professional to locate and non-invasively determine the setting of an implanted valve. After the valve has been located and the setting of the valve determined, the valve may be re-adjusted non-invasively.

There are three tools: a locator tool, an indicator tool and an adjustment tool. The locator tool allows the physician to locate the adjustable valve of interest and align the locator tool with a specific orientation of the valve. The indicator tool indicates the current setting of the adjustable valve and confirms new settings of the valve after the new settings have been implemented. The adjustment tool interacts magnetically with the implanted adjustable valve to couple with a movable internal element to change the setting of the valve. The indicator tool and the adjustment tool physically cooperate with the locator tool to accomplish the respective functions of the tools.

In this invention a hand held indicator tool allows instant determination of the device setting with no requirement for using x-rays. This is accomplished in the present invention by providing a locator tool with an opening that allows tactile determination of the implanted valve's position and orientation. In the preferred embodiment, the indicator tool in this invention is keyed to the locator tool so that it can only be inserted in a correct orientation with respect to the locator tool that has previously been aligned with the valve. The "keyed" relationship minimizes the possibility of erroneous readings of the valve setting.

In the current invention, the adjuster tool is inserted into the locator tool. The adjustment tool couples an external magnetic field to the magnet of the valve to switch the valve through a variety of pressure/flow characteristics. The adjuster tool rotates through a series of "detents" corresponding with setting positions on the valve. As the adjuster tool rotates, the user feels a click when the adjuster tool is aligned with a position of the valve as a positive tactile indication the user that a setting position has been reached. In the current invention, mechanical stops in the tool mirror mechanical stops inside the implanted valve at the range limit of rotating base of the valve. This helps prevent the user from improperly adjusting the valve.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
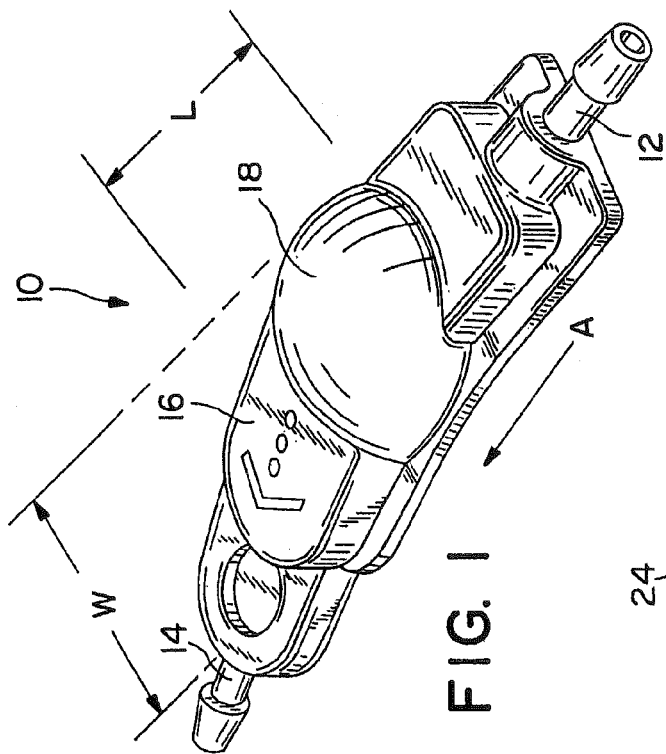
FIG. 1 is a perspective view of an adjustable flow control valve.

Example embodiments will now be described more fully with reference to the accompanying drawings.

The invention comprises three tools, a locator tool 26, an indicator tool 28 and an adjustment tool 30. Although these tools are intended to be used cooperatively in a sequential way, it is clear and within the scope of the invention that they may also be used individually are in paired relationships as will be explained hereafter.

The locator tool is shown in FIGS. 4-7 generally labeled 26. Locator tool 26 allows the physician to locate the adjustable valve 10 of interest and align the locator tool 26 with a specific orientation of the valve 10.

Locator tool 26 has a substantially planar deck 32 and a substantially cylindrical tube 34. The outer edge 36 of deck 32 is attached to the inner surface 38 of tube 34. Tube 34 has in inner diameter D. Tube 34 has an upper surface 40. Deck 32 has a locator central axis 42. Deck 32 has a locator central opening 44 extending entirely therethrough. In the preferred embodiment, locator central axis 42 extends through a portion of locator central opening 44. In addition, locator central opening 44 has a shape as will be described below such that it allows an orientation to be ascribed to it. Deck 32 also has an arrow 46 or other means for pointing out the preferred direction of orientation of the locator tool 26.

Tube 34 preferably has a slot 48 on its inner surface 38 that extends into the material of tube 34 from the upper surface 40 downward at substantially a right angle to the plane of deck 32. Slot 48 is intended to interact with the indicator tool 28 as will be described hereafter.

Figure 6:
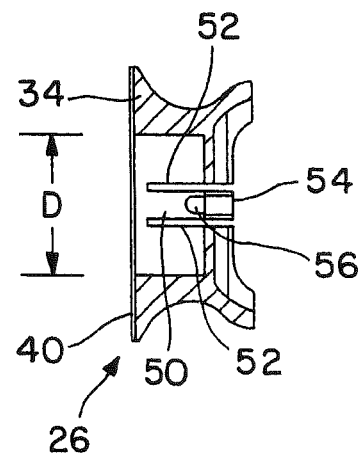
FIG. 6 is a side cross-sectional view of the locator tool of FIG. 4.
Figure 7:
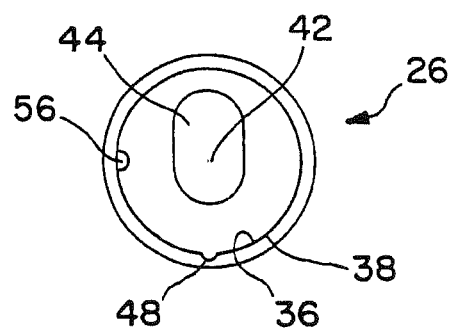
FIG. 7 is a bottom view of the locator tool of FIG. 4.
Figure 8:
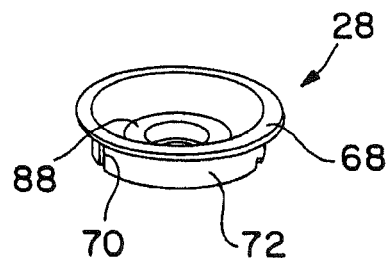
FIG. 8 is a perspective view of the indicator tool of the present invention.
Figure 9:
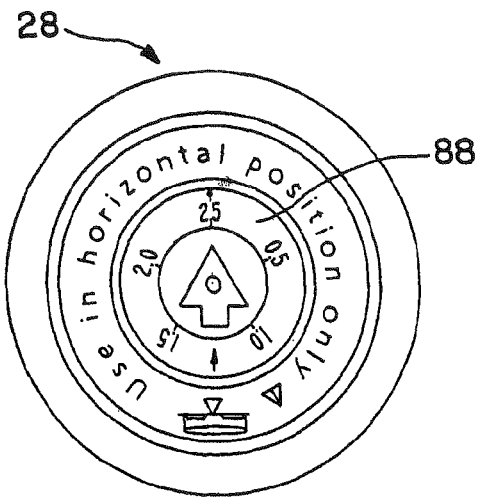
FIG. 9 is a top view of the indicator tool of FIG. 8.
Figure 10:
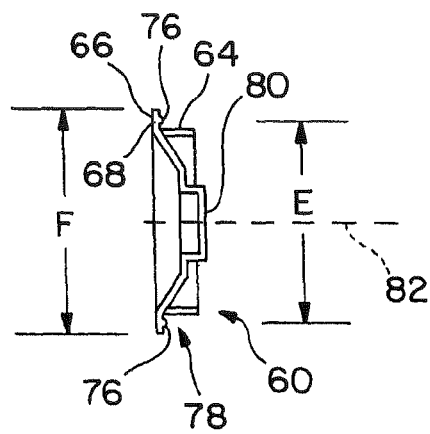
FIG. 10 is a side cross-sectional view of the indicator tool of FIG. 8.
Figure 11:
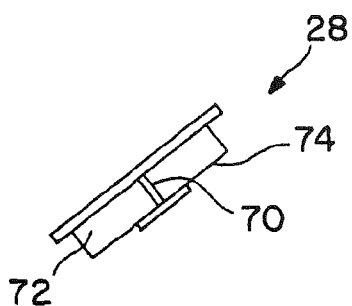
FIG. 11 is a side view of the indicator tool of FIG. 8.
Figure 12:
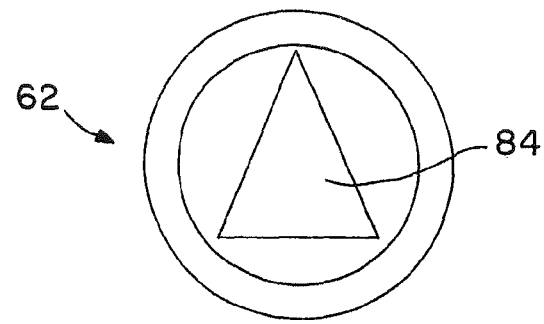
FIG. 12 is a top view of the compass of the indicator tool of FIG. 8.
Figure 13:
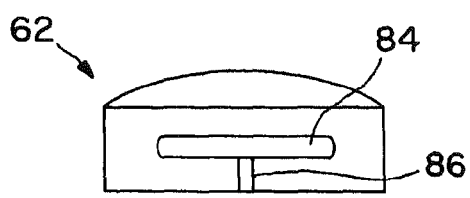
FIG. 13 is a side view of the compass of FIG. 12.
Figure 14:
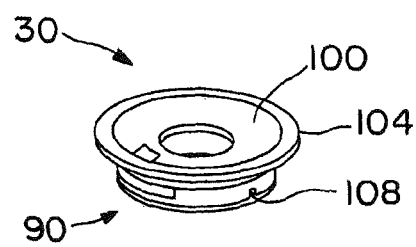
FIG. 14 is a perspective view of the adjustment tool of the present invention.
Figure 15:
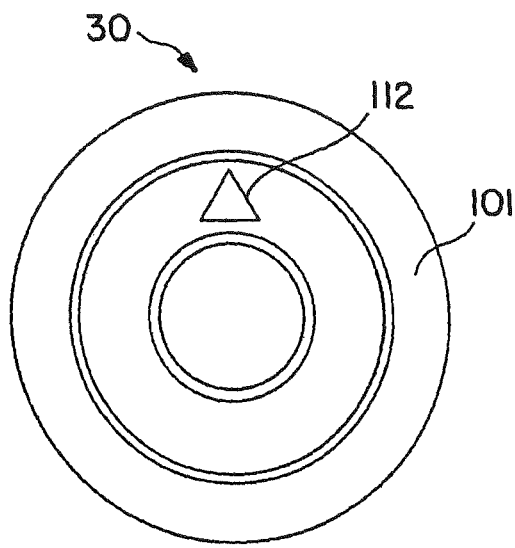
FIG. 15 is a top view of the adjustment tool of FIG. 14.
Figure 16:
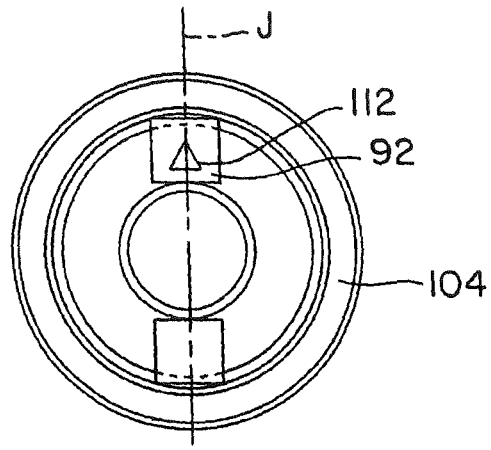
FIG. 16 is a bottom view of the adjustment tool of FIG. 14.
Figure 17:
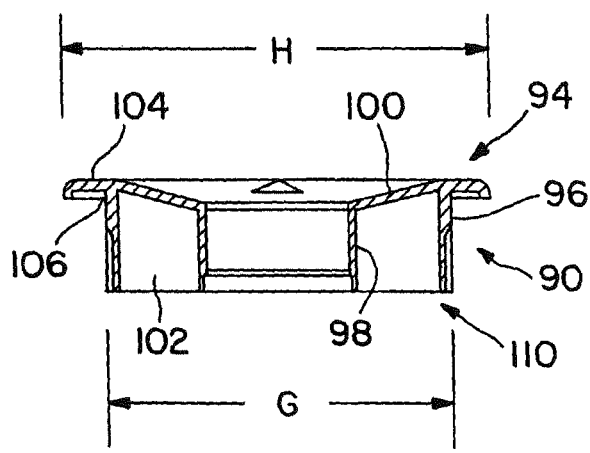
FIG. 17 is a side cross-sectional view of the adjustment tool of FIG. 14 without the magnet in place.
Figure 18:
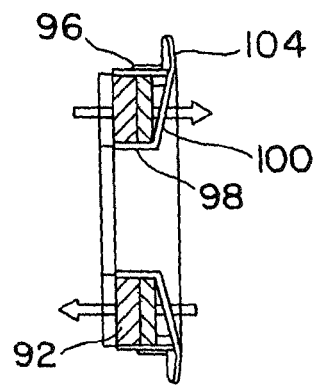
FIG. 18 is a side cross-sectional view of the adjustment tool of FIG. 14 with the magnet in place.

In the preferred embodiment, as seen in FIG. 6, tube 34 has a tab 50 that extends as part of "wall" of tube 34. Tab 50 is formed between two side slots 52 and a bottom slot 54 that extend entirely through the material of tube 34. Tab 50 preferably extends along tube 34 in a direction substantially perpendicular to the plane of deck 32.

A protrusion 56 extends inwardly from the bottom of tab 50 into the central portion of tube 34. Because tab 50 is attached to the main body of tube 34 only at its upper dimension, tab 50 is biased to remain positioned within the dimensions of the "wall" of tube 34. If protrusion 56 is pushed outwardly, for example with contact with the adjustment tool 30 as will be explained hereafter, tab 50 is biased to resist such displacement and to tend to move itself and protrusion 56 back to their original unstressed position.

Figure 4:
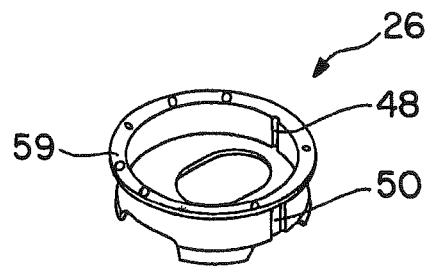
FIG. 4 is a perspective view of the locator tool of the present invention.
Figure 4A:
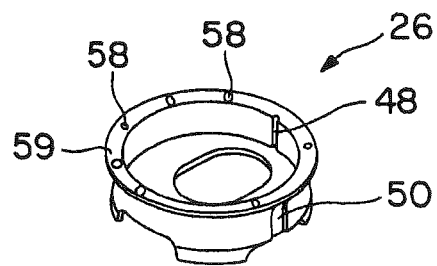
FIG. 4a is a perspective view of an alternate embodiment of the locator tool of the present invention.
Figure 5:
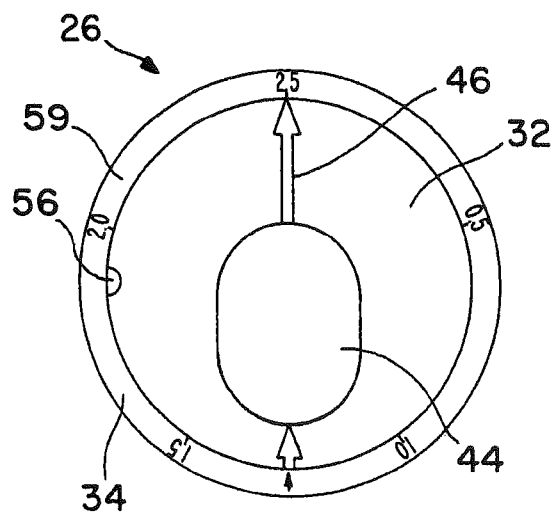
FIG. 5 is a top view of the locator tool of FIG. 4.

In an alternate embodiment shown in FIG. 4a, the upper surface 40 of tube 34 has a series of indentations 58 located at certain locations around the upper surface 40. The purpose of these indentations 58 will be explained in more detail hereafter.

An index 59 may be placed on the upper surface 40 of tube 34. Index 59 visually indicates the settings of valve 10 when locator tool 26 is correctly oriented with valve 10.

Figure 2:
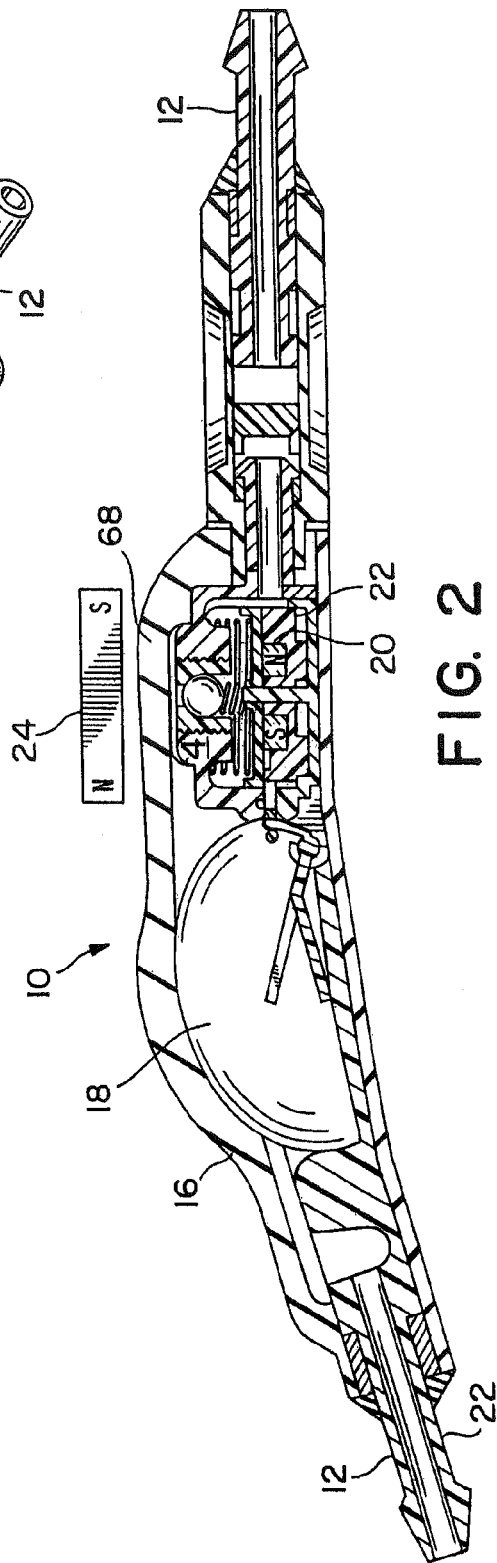
FIG. 2 is a side cross-sectional view of the valve of FIG. 1.
Figure 3A:
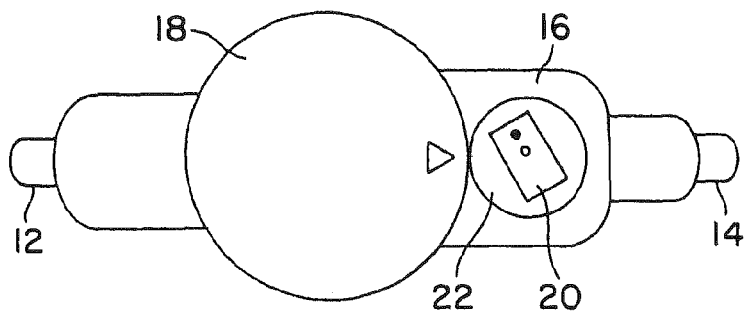
FIGS. 3A-3E are top x-ray views of the valve of FIG. 1 with the magnet in a variety of orientations corresponding to varying levels of pressure/flow through the valve.
Figure 3B:
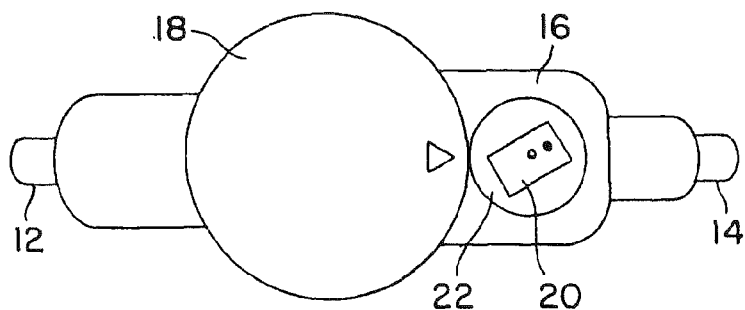
Figure 3C:
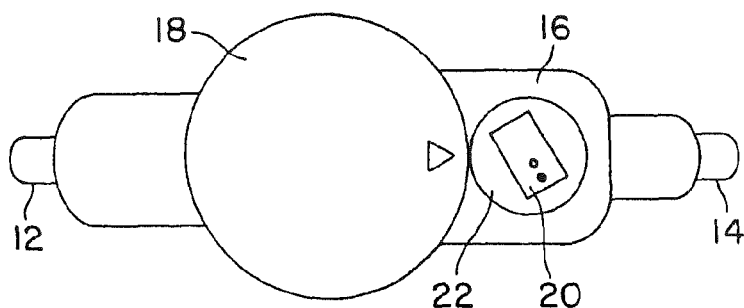
Figure 3D:
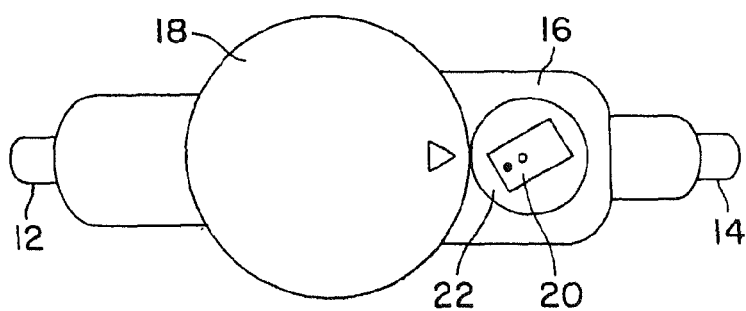
Figure 3E:
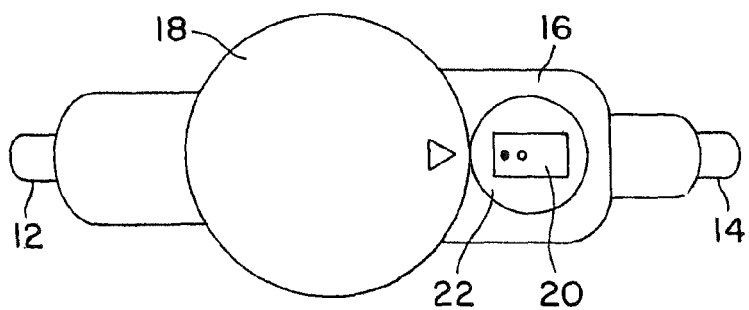

In many adjustable valves, such as the valve 10 shown in U.S. Pat. No. 5,637,083, the dome 18 of the valve 10 has a direction of orientation. For example, in the valve 10 shown in the '083 patent, the width "W" of the dome 18 is narrower transverse to the direction of fluid flow "A" than is the length "L" of the dome 18 along the direction of fluid flow "A" as shown in FIGS. 1-3. This difference in dimensions allows the dome 18 itself to have a direction of orientation. In this case, the elongated dimension of the dome 18 is aligned with the direction of fluid flow "A" through the valve 10.

In use, the valve 10 is implanted under the patient's skin on the skull. The skin around the skull is relatively thin. Thus, the physician can palpate the valve 10 through the skin. By feeling the dome 18 and other physical characteristics of the valve 10, the physician can identify the orientation of the dome 18.

Figure 19:
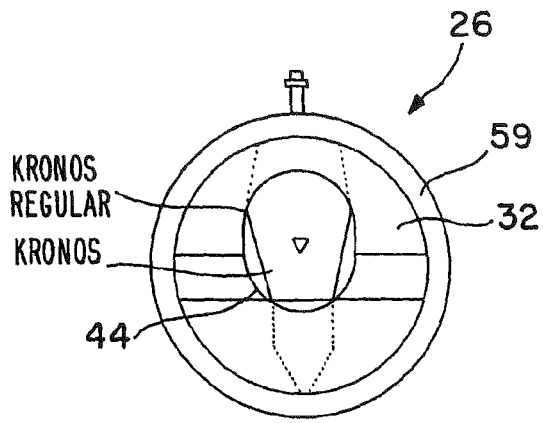
FIG. 19 is a top view of the locator tool of FIG. 4 in position on an adjustable valve.

Locator central opening 44 is slightly larger than and essentially the same shape as the dome 18 on the adjustable valve 10. As a result, locator central opening 44 also has a direction of orientation that will correspond to the orientation of the dome 18. Once the physician has palpated the dome 18 of the implanted valve 10 and determined its orientation, he sets the locator tool 26 over the dome 18. The dome 18 will extend into the locator central opening 44. Because the dome 18 and the locator central opening 44 have similar shape, by rotating the deck 32 about the locator central axis 42, the physician will eventually bring the dome 18 and the locator central opening 44 into alignment. This will occur where the clearance between the locator central opening 44 and the dome 18 is minimized. When this alignment occurs, the locator tool 26 will be aligned with the valve 10 (FIG. 19). In this position, the arrow 46 will point in the direction of fluid flow through the valve 10.

As described, in the preferred embodiment, the locator central opening 44 has a similar shape to the dome 18. In particular, the locator central opening 44 has an elongated shape that corresponds to the shape of the dome 18. Although this is the preferred shape of locator central opening 44, other shapes may also be used. For example, if dome 18 has a different shape, cylindrical, circular, spherical, slot-shaped, diamond, triangular, rectangular or irregular, to name but a few of the many possible choices that will occur to those skilled in the art, locator central opening 44 would also have a corresponding shape. The key here is to have a shape for the locator central opening 44 that allows the locator tool 26 to be oriented to and aligned with the valve 10 in a precise predictable manner. Additionally, in the preferred embodiment, locator central opening 44 should allow the physician to palpate the implanted valve 10 through the locator central opening 44.

The indicator tool is shown in FIGS. 8-13 generally labeled 28. The indicator tool 28 indicates the current setting of the adjustable valve 10 and confirms new settings of the valve 10 after the new settings have been implemented.

Indicator tool 28 has two main parts: an indicator central body 60 and a compass 62. Indicator central indicator central body 60 has an annular portion 64. Annular portion 64, in the preferred embodiment, is cylindrical with an outer diameter "E" that is slightly less than the inner diameter "D" of tube 34. An indicator lip 66 extends outward from the upper surface 68 of indicator central body 60. The outer diameter "T" of indicator lip 66 is larger than the inner diameter "D" of tube 34.

In the preferred embodiment corresponding to the embodiment of the locator tool 26 having a slot 48 on the inner surface 38 of tube 34, central body 60 has a ridge 70 extending outward from its outer surface 72. Ridge 70 extends upward from the bottom 74 of the central body 60 at substantially a right angle to indicator lip 66. Ridge 70 is dimensioned to slide into slot 48 so that the interaction between slot 48 and ridge 70 will keep central body 60 from rotating with respect to the locator tool 26 in use as will be described hereafter.

In an embodiment corresponding to the embodiment of the locator tool 26 having indentations 58 described above, protrusions 76 extend downward from the underside 78 of lip 56. These protrusions 76 are positioned to correspond to the indentations 58 on the upper surface 40 of tube 34. In this way, when indicator tool 28 is used with locator tool 26 and the protrusions 76 are aligned with the indentations 58, indicator tool 28 is precisely oriented with locator tool 26 and central body 60 is inhibited from rotating with respect to locator tool 26 as will be described hereafter.

Indicator central body 60 has a indicator central opening 80 extending around a indicator central axis 82. A compass 62 is fixed in place in indicator central opening 80. Compass 62 has a magnetized pointer 84 that rotates around a spindle 86 so that pointer 84 may align itself with magnetic fields it encounters.

Although the preferred embodiment has compass 62 fixed in central opening 80, in another embodiment, indicator central body 60 has no central opening. In this embodiment, compass 62 may be attached directly to indicator central body 60 by means such as adhesives as will be clear to those skilled in the art.

An index 88 is affixed to the upper surface 68 of indicator central body 60 around compass 62. Index 88 indicates the possible positions of the mechanism of the adjustable valve 10 corresponding to the different settings of the valve 10.

In use, after the orientation of the valve 10 has been established by locator tool 26 as described above, the indicator central body 60 of indicator tool 28 is placed within tube 34 of locator tool 26. Because the outer diameter "E" of the annular portion 64 of the indicator central body 60 is slightly smaller than and is conformal to the inner diameter of tube 34, indicator central body 60 should pass into tube 34 until lip 56 contacts and rests upon the upper surface 40 of tube 34.

Figure 20:
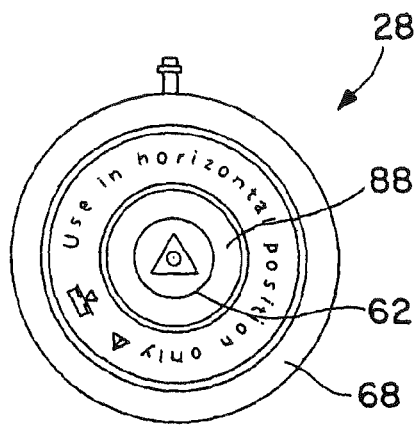
FIG. 20 is a top view of the indicator tool of FIG. 8 in place in the locator tool of FIG. 19.

In the preferred embodiment, ridge 70 will align with and interact with slot 48 to precisely orient indicator tool 28 with locator tool 26. In the alternate embodiment, indicator lip 66 is rotated until protrusions 76 are in contact with the indentations 58 in locator tool 26. In either configuration, locator tool 26 and indicator tool 28 are aligned and oriented with respect to the preferred orientation of valve 10 (FIG. 20). Pointer 84 will then interact with the magnet 20 of valve 10 so that pointer 84 will align itself with the magnet 20 of valve 10. This will cause pointer 84 to point to a spot on index 88. Where the pointer 84 points to on index 88 indicates the position of the magnet 20 of the valve 10. The position of the magnet 20 indicates the setting of the valve 10.

The adjustment tool is shown in FIGS. 14-18 generally labeled 30. The adjustment tool 30 interacts magnetically with the implanted adjustable valve 10 to couple with the magnet 20 fixed to a movable internal element in valve 10 to change the setting of the valve 10.

Adjustment tool 30 has two main parts: an adjustment central body 90 and a magnet 92. Magnet 92 performs the function of the external magnet 24 described above. Adjustment central body 90 has an adjustment annular portion 94 made up of an outer wall 96, an inner wall 98 and an upper wall 100. Adjustment annular portion 94 has an annular open area 102 between outer wall 96 and inner wall 98 and opposite upper wall 100. In the preferred embodiment, outer wall 96 is cylindrical with an outer diameter "G" that is slightly less than the inner diameter "D" of tube 34. An adjustment lip 104 extends outward from the upper edge 106 of adjustment central body 90. The outer diameter "H" of adjustment lip 104 is larger than the inner diameter "D" of tube 34. In the preferred embodiment, adjustment lip 104 is made of a clear material so that index 59 may be viewed through adjustment lip 104 when adjustment tool 30 is in place on locator tool 26.

Adjustment central body 90 has a series of indentations 108 near its bottom 110. These indentations 108 are located a distance from adjustment lip 104 and configured so that the indentations 108 will interact with protrusion 56 on tab 50 when adjustment tool 30 is mated to locator tool 26 as described below. Indentations 108 are spaced around the periphery of adjustment central body 90 corresponding to the location of the settings of the valve 10.

Magnet 92 is fixed in place in within adjustment central body 90. Magnet 92 has a north pole N and a south pole S aligned along an axis "J" of adjustment central body 90. Axis J is aligned with a direction indicator which is preferentially in the form of an arrow 112.

Figure 21:
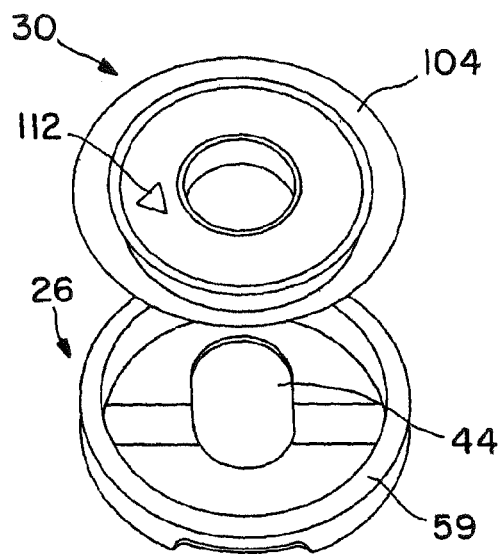
FIG. 21 is a perspective view of the adjustment tool of FIG. 14 being moved into contact with the locator tool of FIG. 19.
Figure 22:
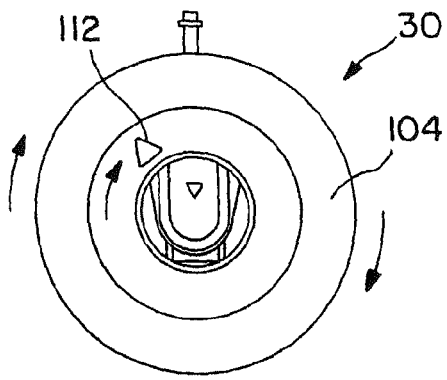
FIG. 22 is a top view of the adjustment tool of FIG. 21 in place in the locator tool of FIG. 19.

In use, the orientation of the valve 10 is first established by locator tool 26 and indicator tool 28 as described above. Then, the adjustment tool 30 is used, as necessary or as desired, to change the position of the magnet 20 and consequently the setting of the valve 10. This is done by first removing indicator tool 28 from locator tool 26. Then, adjustment tool 30 is positioned above locator tool 26 with the arrow 112 aligned with the pressure level setting on index 59 determined by the indicator tool 28 (FIG. 21). Maintaining this alignment, the adjustment tool 30 is lowered toward the locator tool 26 until the adjustment central body 90 enters tube 34 and adjustment lip 104 contacts the upper surface 26 of tube 34. At this time, protrusion 56 should interact with one of the indentations 108 on adjustment central body 90 that corresponds to the current setting of the valve 10 (FIG. 22).

In this position, magnet 92 couples with magnet 20 in valve 10. Adjustment central body 90 is then rotated so that the arrow 112 points to the desired setting of valve 10 indicated on index 59. Because magnet 20 is magnetically coupled to magnet 92, as magnet 92 rotates with adjustment central body 90, magnet 20 will also rotate and thereby move to the desired setting of valve 10. As central body 90 rotates, protrusion 56 will be moved out of contact with the indentation 108 corresponding to the last setting of the valve and move against the outer surface outer wall 96 of central body 90. When magnet 92 has moved to the next setting of the valve 10, protrusion 56 should contact the next indentation 108 corresponding to the next setting of the valve 10. The user should feel the protrusion 56 moving into or out of this indentation 108. In this way, the user has tactile confirmation that the adjustment tool 30 has moved to and is aligned with a new valve setting. This process may be repeated as desired until the adjustment tool 30 has moved the magnet 92, and correspondingly the magnet 20, to the new ultimate valve setting.

After the magnet 20 of valve 10 has been moved to a new setting, indicator tool 28 should be used again as described above to confirm that magnet 20 is in the desired position and that, therefore, valve 10 is at the desired valve setting.

In the described preferred embodiment, locator tool 26 is mechanically coupled to either indicator tool 28 or adjustment tool 30 through the interaction of tube 34 and either indicator central body 60 or adjustment central body 90, respectively. In this embodiment, the hollow cylinder formed by tube 34 "captures" the cylindrical bodies of indicator central body 60 or adjustment central body 90 within the central portion of tube 34. Although this is the preferred embodiment, it is clear that locator tool 26 may be mechanically coupled to either indicator central indicator central body 60 or adjustment central body 90 by other means. For example, a cylindrical tube 34 could be "captured" within a downward extending cylinder from indicator tool 28 or adjustment tool 30. In this embodiment, there may also be slots 48 and ridges 70 or other alignment means to orient and align the indicator tool 28 with the locator tool 26.

Alternately, with respect to the interaction between the locator tool 26 and the indicator tool 28, instead to the inner surface 38 of tube 34 and indicator central body 60 both being conformally cylindrical, the inner surface 38 and indicator central body 60 may have other conformal shapes that allow the two tools to be mated together and maintain a desired orientation. For example, the inner surface 38 of tube 34 may be square, rectangular, hexagonal, elliptic or any other shape. Indicator central body 60 would also have a corresponding conformal shape. In this way, when indicator tool 28 is mated with locator tool 26, indicator tool 28 would be precisely located and oriented with respect to locator tool 26. Other means may occur to those skilled in the art.

All such means for mechanically coupling the locator tool 26 to either indicator central indicator central body 60 or adjustment central body 90 are intended to be within the scope of the invention. The key function of such mechanical coupling means is to ensure that the indicator central indicator central body 60 or adjustment central body 90 are aligned with the locator tool 26. Further, whatever the design, it is a key function of the mechanical coupling means to ensure that the magnet 92 of the adjustment central body 90 is allowed to be magnetically coupled to and rotate the magnet 20 of the valve 10 in a controllable fashion.

Further, the interaction of slot 48 or protrusions 76 on tube 34 with ridge 70 or indentations 58 of indicator tool 28, respectively, helps to align the indicator tool 28 with the locator tool 26. Although this is the preferred method of aligning these tools, other ways of aligning the tools will occur to those skilled in the art in addition to the means for mechanically coupling locator tool 26 to indicator tool 28 described above, which provides an alignment of the locator tool 26 and indicator tool 28. These additional means include, but are not limited to, reversing the placement of the slots and ridges or protrusions and detents on the respective tools. In addition, other means of mechanical alignment will occur to those skilled in the art.

Further, another aid in aligning the locator tool 26 and the indicator tool 28 include visual indicators of position on the respective devices. Examples of these visual means to aid in aligning the respective tools include, but are not limited to aligning indicator marks, line, templates or the like on the respective devices.

In addition, locator tool 26 has been described in the preferred embodiment having a locator central opening 44 to allow the physician to palpate the valve 10 through the locator central opening 44. Although this is the preferred embodiment, locator tool 26 may also not have a locator central opening 44. In this embodiment, the physician would align the locator tool 26 with the valve 10 by other means. One such means could be determining the orientation of the valve 10 by palpating the valve 10 and then noting the direction of orientation on the patient's skin by a marking on the patient's skin. Locator tool 26 would then be aligned with the marking on the patient's skin.

In this description, the use of the tools has been described as being cooperative and substantially sequential. So for example, the locator tool 26 is used first to establish an orientation aligned with the valve 10. Thereafter, the indicator tool 28 is used to indicated the current setting of the valve 10. Then, the adjustment tool 30 is used, if needed, to move the valve 10 to a new setting. Finally, the indicator tool 28 is used again to confirm that the new setting is in fact the desired setting.

It is within the scope of the invention to use the locator tool 26 and the indicator tool 28 without ever using adjustment tool 30. In this embodiment of the invention, the information on the current setting of the valve 10 may be sufficient or may be used with some other means to change the setting of the valve 10.

It is also within the scope of the invention to use the locator tool 26 and the adjustment tool 30 without using the indicator tool 28. In this embodiment of the invention, the setting of the valve 10 would be determined by other means, such as by x-ray, or inferred. In any case, the setting of the valve 10 would be determined without using the indicator tool 28. Thereafter, the adjustment tool 30 would operate as described above to change the setting of the valve 10.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A locator tool for determining an orientation of a valve implanted in a patient having a tactile physical characteristic that indicates a specific orientation of the implanted valve, the locator tool comprising:
    an indicator configured to indicate an orientation of the implanted valve; and
    a substantially planar deck having a first engagement surface configured to engage the patient relative to the tactile physical characteristic of the implanted valve and an opposed second surface, the deck defining a locator opening extending entirely through the deck from the first surface to the second surface, the locator opening having a continuous perimeter edge of the locator opening shaped and configured to allow an orientation to be ascribed to it and to substantially correspond to an outer edge of the tactile physical characteristic,
    wherein the locator opening is capable of overlying and aligning with the outer edge of the tactile physical characteristic such that space between the locator opening and the outer edge of the tactile physical characteristic is minimized to indicate alignment between the opening and the tactile physical characteristic,
    wherein the locator opening is shaped to have a direction of orientation that will correspond to a directional orientation of the implanted valve upon aligning the locator opening with the tactile physical characteristic,
    wherein upon alignment, the indicator indicates the orientation of the implanted valve.

2. The locator tool of claim 1, wherein the indicator is a visual indicator to indicate the orientation of the implanted valve.

3. The locator tool of claim 2, wherein the visual indicator is an arrow.

4. The locator tool of claim 3, wherein the arrow is located on the deck.

5. The locator tool of claim 1, wherein the locator tool further includes a substantially cylindrical tube having an inner surface, an outer edge of the deck being attached to the inner surface of the tube.

6. The locator tool of claim 5, wherein the tube has an upper annular surface having an index placed thereon, the index being configured to visually indicate a setting of the implanted valve.

7. The locator tool of claim 1, wherein the locator opening has an elongated shape extending along an axis to provide a direction of orientation that corresponds to the outer edge of the tactile physical characteristic and the deck has a locator central axis wherein the locator central axis extends through a portion of the elongated locator opening.

8. The locator tool of claim 5, further comprising an indicator tool configured to be removably received within an inner diameter of the tube and configured to indicate a setting of the implanted valve.

9. The locator tool of claim 8, wherein the indicator tool is keyed to the tube of the locator tool.

10. The locator tool of claim 9, wherein the indicator tool is keyed to the tube by way of a recess and a corresponding protrusion.

11. A system for determining an orientation of an implanted medical device having a tactile physical characteristic that indicates a specific orientation of the implanted medical device, comprising:
    a locator tool including;
    an indicator configured to indicate an orientation of the implanted medical device;
    a deck having a first engagement surface configured to be engaged relative to the tactile physical characteristic of the implanted medical device and an opposed second surface, the deck defining a locator opening extending entirely through the deck from the first surface to the second surface, an edge of the locator opening shaped to substantially correspond to an outer edge of the tactile physical characteristic; and
    a substantially cylindrical tube having an inner surface, an outer edge of the deck being attached to the inner surface of the tube;
    wherein the locator opening is capable of overlying and aligning with the outer edge of the tactile physical characteristic such that space between the locator opening and the outer edge of the tactile physical characteristic is minimized to indicate alignment between the opening and the tactile physical characteristic,
    wherein upon alignment, the indicator indicates the orientation of the implanted medical device; and
    an adjustment tool configured to be removably received within an inner diameter of the tube and configured to adjust a setting of an adjustable implanted valve located within the implanted medical device.

12. The system of claim 11, wherein the tube defines a flexible tab having a protrusion extending therefrom, wherein the protrusion is configured to interact with an indentation in a body of the adjustment tool.

13. A locator tool for determining an orientation of a magnetic adjustable valve implanted in a patient, where the implanted valve has an engageable subdermal surface that indicates a specific orientation of the implanted valve, the locator tool comprising:
    a substantially planar deck having a first engagement surface configured to engage the engageable subdermal surface of the patient and an opposed second surface, the deck defining a locator opening extending entirely through the deck from the first engagement surface to the second surface, the locator opening defining a closed perimeter edge shaped and configured to allow an orientation to be ascribed to it and to substantially correspond to the engageable subdermal surface, wherein the locator opening is capable of overlying and aligning with the engageable subdermal surface such that the space between the locator opening and the engageable subdermal surface is minimized to indicate alignment between the locator opening and the engageable subdermal surface to indicate an orientation of the implanted valve and a direction of fluid flow through the implanted valve;

wherein the locator opening is shaped to have a direction of orientation that will correspond to an orientation of the implanted valve upon aligning the locator opening with the engageable subdermal surface.

14. The locator tool of claim 13, wherein the deck extends to an outer edge having a cylindrical wall extending from the outer edge, where the cylindrical wall has an inner diameter configured to removably receive either an indicator tool or an adjustment tool.

15. The locator tool of claim 14, wherein the deck further includes a visual indicator located on the deck to indicate the orientation of the implanted valve upon the locator opening aligning with the engageable subdermal surface.

16. The locator tool of claim 15, wherein the indicator tool and the adjustment tool are each configured to be rotationally keyed relative to the cylindrical wall.

17. A locator tool for determining an orientation of a valve implanted in a patient having a tactile physical characteristic that indicates a specific orientation of the implanted valve, the locator tool comprising:

a planar deck having a first engagement surface configured to be placed on the patient relative to the tactile physical characteristic of the implanted valve and an opposed second surface, the deck defining a locator opening extending entirely through the deck from the first engagement surface to the second surface, the locator opening having a non-circular elongated shape extending along an axis to substantially correspond to an outer edge of the tactile physical characteristic, wherein the non-circular elongated opening is capable of overlying and aligning with the outer edge of the tactile physical characteristic to indicate alignment between the locator opening and the tactile physical characteristic;

a visual indicator configured to indicate an orientation of the implanted valve upon the locator opening aligning with the tactile physical characteristic; and a raised perimeter wall extending about an outer edge of the planar deck having an inner dimension configured to removably receive an indicator tool or an adjustment tool;

wherein the locator opening is shaped to have a direction of orientation that will correspond to an orientation of the implanted valve upon aligning the locator opening with the tactile physical characteristic.

18. The locator tool of claim 17, wherein the indicator tool is configured to indicate a current setting of the implanted valve.

19. The locator tool of claim 17, wherein the adjustment tool is configured to adjust a setting of the implanted valve.

* * * * *